(12) United States Patent
Fard et al.

(10) Patent No.: US 12,139,467 B2
(45) Date of Patent: Nov. 12, 2024

(54) METHODS OF SYNTHESIZING CANNABIELSOIN AND ANALOGS THEREOF

(71) Applicant: Canopy Growth Corporation, Smiths Falls (CA)

(72) Inventors: Mahmood Azizpour Fard, Smiths Falls (CA); Ben Geiling, Smiths Falls (CA); Mohammadmehdi Haghdoost Manjili, Smiths Falls (CA)

(73) Assignee: Canopy Growth Corporation, Smiths Falls (CA)

( * ) Notice: Subject to any disclaimer, the term of this patent is extended or adjusted under 35 U.S.C. 154(b) by 107 days.

(21) Appl. No.: 17/639,302

(22) PCT Filed: Jul. 26, 2021

(86) PCT No.: PCT/CA2021/051040
§ 371 (c)(1),
(2) Date: Feb. 28, 2022

(87) PCT Pub. No.: WO2022/020944
PCT Pub. Date: Feb. 3, 2022

(65) Prior Publication Data
US 2023/0146330 A1    May 11, 2023

Related U.S. Application Data

(60) Provisional application No. 63/057,134, filed on Jul. 27, 2020.

(51) Int. Cl.
*C07D 307/91* (2006.01)
(52) U.S. Cl.
CPC .................. *C07D 307/91* (2013.01)

(58) Field of Classification Search
None
See application file for complete search history.

(56) References Cited

FOREIGN PATENT DOCUMENTS

WO    WO 2018/160827 A1    9/2018

OTHER PUBLICATIONS

Lumir Ondrej Hanus et al. "Phytocannabinoids: A unified critical inventory." *Natural Product Report*, 33, 1357-1392, Dec. 12, 2016.
International Search Report and Written Opinion dated Oct. 5, 2021, in International Application No. PCT/CA2021/051040.
F.J.E.M Kuppers et al. "Cannabis VIII. Pyrolysis of cannabidiol. Structure Ellucidation of Main Pyrolytic Product." *Tetrahedron*, vol. 29, 18, 2797-2802, 1973.
David Uliss et al. "Stereospecific Intramolecular Epoxide Cleavage by Phenolic Anion. Synthesis of Novel and Biologically active Cannabinoids." Journal of American Chemical Society, 96:23, Nov. 13, 1974.

*Primary Examiner* — Samantha L Shterengarts
(74) *Attorney, Agent, or Firm* — Knobbe, Martens, Olson & Bear, LLP

(57) ABSTRACT

Disclosed are methods for synthesizing cannabielsoin (CBE) and or analogs thereof. In particular, the present disclosure provides methods for synthesizing CBE or analogs thereof comprising steps of providing a cannabinoid composition that comprises cannabidiol (CBD) or analogs thereof; combining the cannabinoid composition with an agent comprising a ketone functional group; and contacting the cannabinoid composition with an oxidizing agent or exposing the cannabinoid composition to electromagnetic radiation.

20 Claims, 4 Drawing Sheets

FIG. 1A
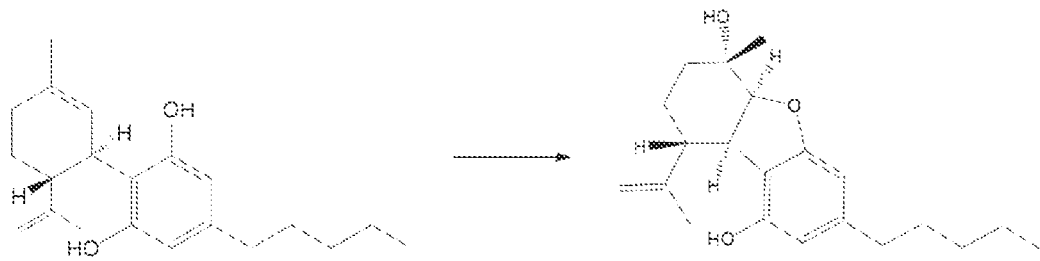
FIG. 1B
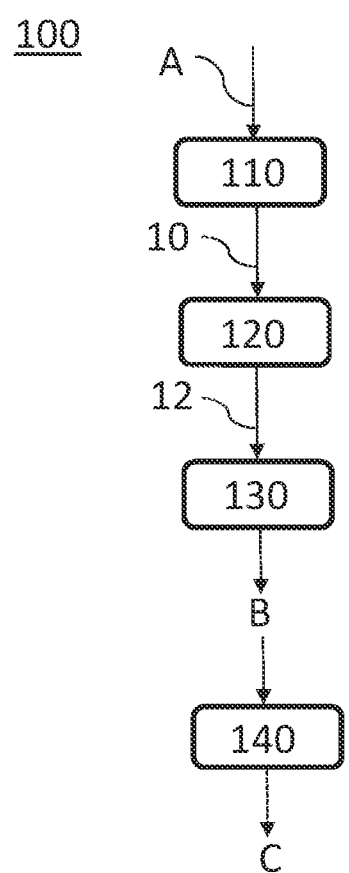
FIG. 1

FIG. 2A
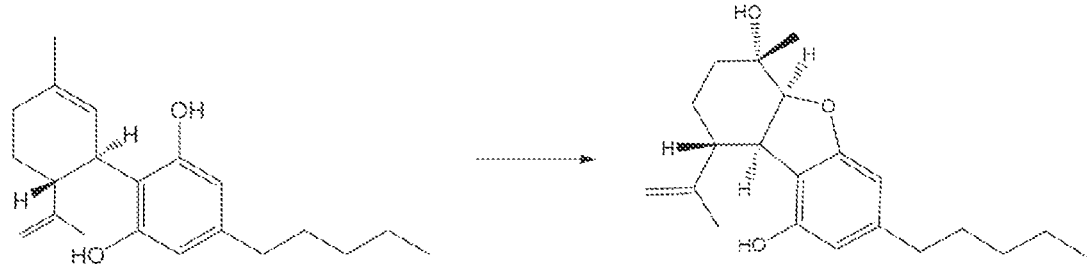
FIG. 2B
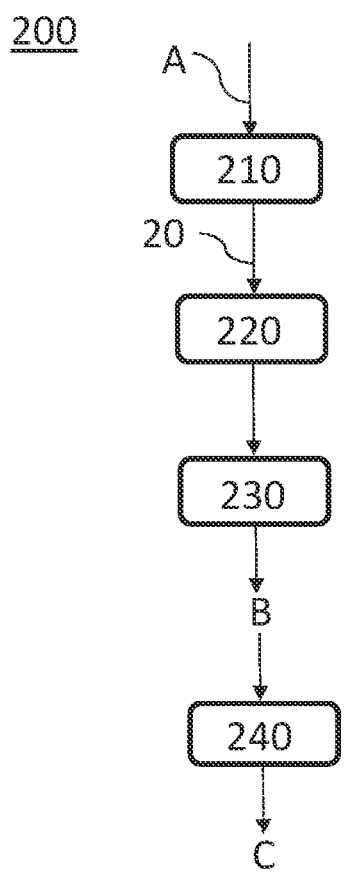
FIG. 2

FIG. 3A
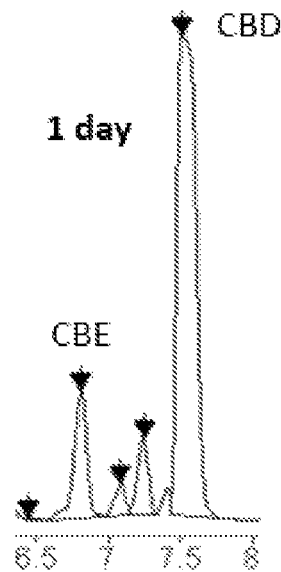
FIG. 3B
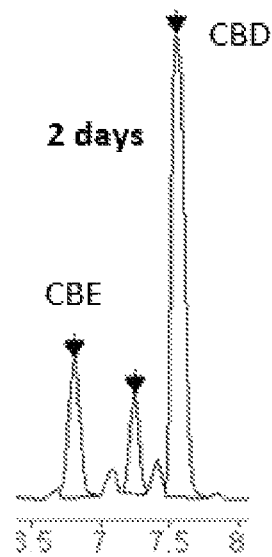
FIG. 3C
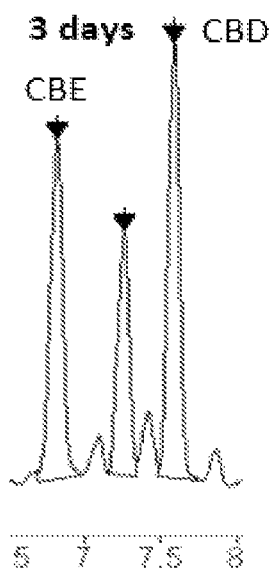
FIG. 3D
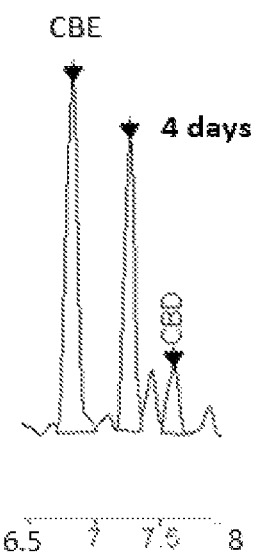
FIG. 3

METHODS OF SYNTHESIZING CANNABIELSOIN AND ANALOGS THEREOF

CROSS-REFERENCE TO RELATED APPLICATIONS

This application is a national stage filing under 35 U.S.C. 371 of International Application No. PCT/CA2021/051040, which is hereby incorporated by reference in its entirety, which claims priority to and benefit of U.S. Provisional Patent Application Ser. No. 63/057,134 filed on Jul. 27, 2020, which is hereby incorporated by reference in its entirety.

TECHNICAL FIELD

The present disclosure generally relates to methods of synthesizing cannabinoids. In particular, the present disclosure relates to methods for synthesizing cannabielsoin (CBE) or analogs thereof from cannabidiol (CBD) or analogs thereof.

BACKGROUND

Cannabinoids can be defined in pharmacological terms as a class of compounds that can bind specific cannabinoid-receptors found in central nervous-system tissues and peripheral nervous-system tissues of mammals. The interactions between cannabinoids and these receptors are under active investigation by a number of researchers because the resultant physiologic effects are demonstrably important both in medicinal and recreational contexts.

Cannabielsoin (CBE) is a by-product of cannabidiol (CBD) metabolism in both cannabis plants and mammals. Currently, the properties of CBE are not fully understood and, therefore, potential medicinal and recreational applications with CBE have not been extensively explored. However, sourcing CBE as a cannabis-plant isolate is challenging, costly, and a time-consuming process and, therefore, large-scale quantities of high purity CBE are generally unavailable.

Accordingly, efficient and effective methods for producing large quantities of high purity CBE and analogs thereof are desirable.

SUMMARY

The present disclosure relates to methods of synthesizing cannabielsoin and analogs thereof.

In some embodiments, the present disclosure relates to a method for synthesizing cannabielsoin (CBE) or an analog thereof, the method comprising steps of: providing a cannabinoid composition that comprises cannabidiol (CBD) or an analog thereof; combining the cannabinoid composition with an agent comprising a ketone functional group; and contacting the cannabinoid composition with an oxidizing agent to provide a product mixture comprising CBE or an analog thereof.

In an embodiment, the agent comprising a ketone functional group is acetone.

In an embodiment, the oxidizing agent is selected from the group consisting of persulfates, peroxides, peracids and hypochlorites, and in particular potassium monopersulfate.

In some embodiments, the present disclosure relates to a method for synthesizing cannabielsoin (CBE) or an analog thereof, the method comprising steps of: providing a cannabinoid composition that comprises cannabidiol (CBD) or an analog thereof; combining the cannabinoid composition with an agent comprising a ketone functional group; and exposing the cannabinoid composition to electromagnetic radiation to provide a product mixture comprising CBE or an analog thereof.

In an embodiment, the agent comprising a ketone functional group is acetone and the electromagnetic radiation is ultraviolet (UV) radiation.

Other aspects and features of the present disclosure will become apparent to those ordinarily skilled in the art upon review of the following description of specific embodiments.

BRIEF DESCRIPTION OF THE DRAWINGS

FIG. 1 shows a general reaction scheme (FIG. 1A) and a schematic of a method for synthesizing cannabielsoin or analogs thereof from a cannabinoid composition (FIG. 1B), according to select embodiments of the present disclosure.

FIG. 2 shows another general reaction scheme (FIG. 2A) and a schematic of a method for synthesizing cannabielsoin or analogs thereof from a cannabinoid composition (FIG. 2B), according to select embodiments of the present disclosure.

FIG. 3 shows chromatograms of a product mixture obtained from a method of the present disclosure, wherein FIG. 3A shows results obtained after one day; FIG. 3B shows results obtained after two days; FIG. 3C shows results obtained after three days; and FIG. 3D shows results obtained after four days.

DETAILED DESCRIPTION

Figure 4:
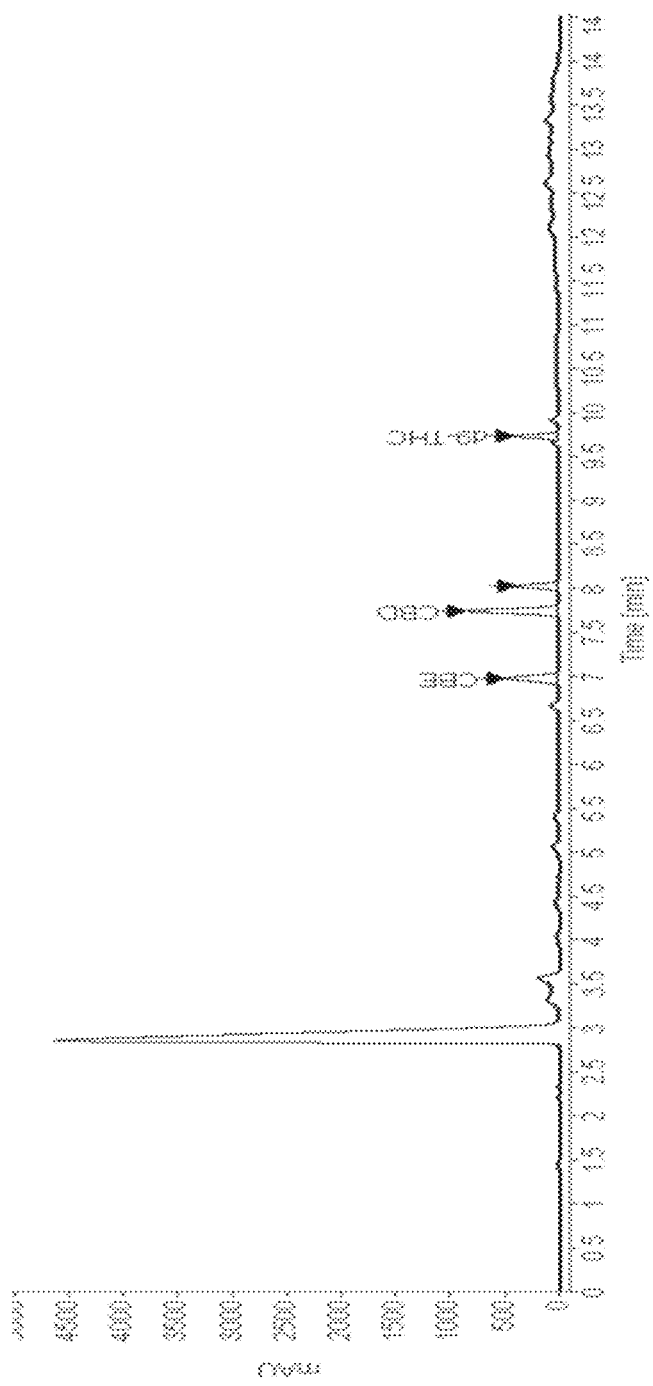
FIG. 4 shows a chromatogram of a product mixture obtained from a method of the present disclosure.

An important aspect of the cannabis industry is having cost-effective access to sufficient quantities of cannabinoids, including those that are less abundant in cannabis plant material.

In many instances, it may be desirable to isolate large quantities of cannabinoids that are present in low quantities in cannabis plant material or cannabis extracts. Further, it may be desirable to prepare cannabinoid analogs and/or homologs as some of these compounds have also been shown to bind to cannabinoid receptors.

The present disclosure relates to methods for synthesizing cannabielsoin (CBE) or analogs thereof. In the context of the present disclosure, the CBE may have the following structure:

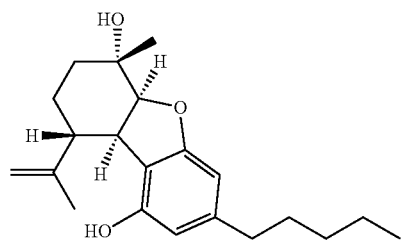 [SMILES: C=C(C)[C@@H]1CC[C@](C)(O)[C@H]2Oc3cc(CCCCC)cc(O)c3[C@@H]12]

As used herein, the term "CBE analog" is intended to refer to a compound that differs at the $R^1$ position in the following structure:

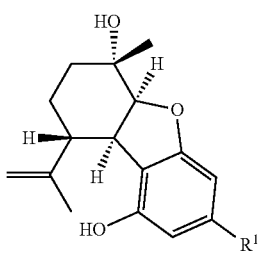

In some embodiments, $R^1$ may be hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$alkyl)-$NR^{2a}R^{2b}$, $(C_0$-$C_4$ alkyl)-aryl, $(C_0$-$C_4$ alkyl)-heteroaryl, $(C_0$-$C_4$alkyl)-cycloalkyl, or $(C_0$-$C_4$alkyl)-heterocycloalkyl, wherein $R^{2a}R^{2b}$ are each independently hydrogen or $C_1$-$C_6$ alkyl. In select embodiments, $R^1$ may be methyl, ethyl, propyl, butyl, heptyl, 1,1-dimethylheptyl, phenylethyl, or phenylvinyl. In select embodiments, $R^1$ is $C_3H_7$ or $C_7H_{15}$.

In the context of the present disclosure, analogs include homologs. The term "homolog" as used herein refers to a group or series of compounds that differ only with respect to the number of repeating units in the alkyl chain on the aryl moiety located at the meta-position with respect to the hydroxyl groups. More specifically, homologs of the present disclosure include alkyl chains on the aryl moiety of the formula —$(CH_2)_{0-11}CH_3$ and the repeating unit in the alkyl chain is methylene (—$CH_2$—). The term homolog is not limited to homologs of naturally occurring cannabinoids and this term includes homologs of semi-synthetic and cannabinoid derivatives.

In one aspect, the present disclosure relates to a method for synthesizing CBE or an analog thereof, the method comprising steps of: providing a cannabinoid composition that comprises cannabidiol (CBD) or an analog thereof; combining the cannabinoid composition with an agent comprising a ketone functional group; and contacting the cannabinoid composition with an oxidizing agent to provide a product mixture comprising CBE or an analog thereof.

As used herein, the term "cannabinoid composition" is intended to refer to a composition that comprises the cannabinoid cannabidiol (CBD) or an analog thereof. Cannabidiol is a major constituent of the phytocannabinoids and generally has the following structure:

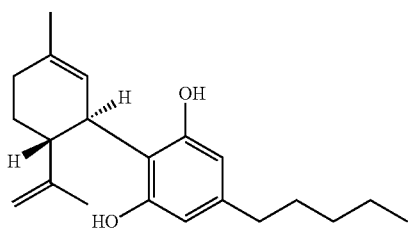 [SMILES: C=C(C)[C@@H]1CCC(C)=C[C@H]1c1c(O)cc(CCCCC)cc1O]

In an embodiment, the cannabinoid composition is a cannabis plant material or an extract, resin, isolate or distillate thereof. In an embodiment, the cannabinoid composition is a partially or a fully synthetic composition. By "a partially or a fully synthetic composition", it is meant that some or all of the components in the composition are provided by chemical synthesis.

In an embodiment, the cannabinoid composition comprises CBD and one or more other cannabinoids or cannabis components (e.g. terpenes).

In an embodiment, the cannabinoid composition is a cannabinoid concentrate. As used herein, the term "cannabinoid concentrate" is meant to refer to a concentrated composition of cannabinoids, such a cannabinoid extract from a plant. Non-limiting exemplary embodiments of a cannabis concentrate include a cannabis distillate, a cannabis isolate, a cannabis oil, or any other type of extract containing one or more cannabinoids. In an embodiment, the cannabis concentrate is a cannabis distillate or isolate dissolved in a carrier solvent, such as for example coconut oil or MCT oil.

In an embodiment, the cannabinoid concentrate comprises at least 5 wt % CBD or an analog thereof, more particularly at least 10 wt % CBD or an analog thereof, and more particularly still at least 25 wt % CBD or an analog thereof. In an embodiment, the cannabinoid concentrate comprises at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 96 wt %, at least 97 wt %, at least 98 wt %, at least 99 wt %, or more CBD or an analog thereof. In select embodiments, the cannabinoid concentrate comprises at least 75 wt % CBD or an analog thereof. In select embodiments, the cannabinoid concentrate comprises at least 90 wt % CBD or an analog thereof. In select embodiments, the cannabinoid concentrate comprises at least 99 wt % CBD or an analog thereof. In an embodiment, the cannabinoid concentrate is a pure CBD composition comprising about 100% CBD.

In an embodiment, the cannabinoid composition comprises one or more CBD analogs having the structure:

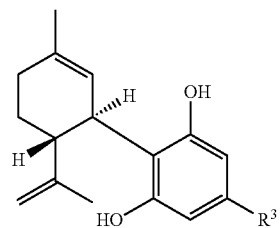

In some embodiments, $R^3$ may be hydrogen, $C_1$-$C_2$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$alkyl)-$NR^{2a}R^{2b}(C_0$-$C_4$ alkyl)-aryl, $(C_0$-$C_4$ alkyl)-heteroaryl, $(C_0$-$C_4$alkyl)-cycloalkyl, or $(C_0$-$C_4$alkyl)-heterocycloalkyl, wherein $R^{2a}R^{2b}$ are each independently hydrogen or $C_1$-$C_6$ alkyl. In select embodiments, $R^3$ may be methyl, ethyl, propyl, butyl, heptyl, 1,1-dimethylheptyl, phenylethyl, or phenylvinyl. In select embodiments, $R^3$ is $C_3H_7$ or $C_7H_{15}$.

In an embodiment, the cannabinoid composition comprises CBD and one or more CBD analogs. In such embodiments, the product mixture may comprise both CBE and one or more CBE analogs. The ratio of CBE:CBE analog may for example, and without limitation, be between 1000:1 and 1:1000. In an embodiment, the ratio of CBE:CBE analog may be about 1000:1, about 500:1, about 250:1, about 100:1, about 75:1, about 50:1, about 25:1, about 10:1, about 5:1, about 4:1, about 3:1, about 2:1, about 1:1, about 1:2, about 1:3, about 1:4, about 1:5, about 1:10, about 1:25, about 1:50, about 1:75, about 1:100, about 1:250, about 1:500, or about 1:1000.

In some embodiments of the present disclosure, the cannabinoid composition is substantially free of CBE. The term "substantially free" is used herein to refer to minimal amounts of CBE present within the cannabinoid composition, such as between about 0 and 10 weight percent ("wt %") of the CBE relative to all other compounds within the cannabinoid composition. In some embodiments, the cannabinoid composition may comprise between about 0 wt % and about 5 wt % CBE, between about 0 wt % and about 1 wt % CBE, between about 0 wt % and 0.1 wt % CBE, between about 0 wt % and 0.01 wt % CBE and between about 0 wt % and 0.001 wt % CBE. In some embodiments, the cannabinoid composition is free of CBE.

As used herein, the term "cannabinoid" refers to: (i) a chemical compound belonging to a class of secondary compounds commonly found in plants of genus cannabis, (ii) synthetic cannabinoids and any enantiomers thereof; and/or (iii) one of a class of diverse chemical compounds that may act on cannabinoid receptors such as CB1 and CB2.

In select embodiments of the present disclosure, the cannabinoid is a compound found in a plant, e.g., a plant of genus cannabis, and is sometimes referred to as a phytocannabinoid. There are at least 113 different cannabinoids isolated from cannabis, exhibiting varied effects.

In select embodiments of the present disclosure, the cannabinoid is a compound found in a mammal, sometimes called an endocannabinoid.

In select embodiments of the present disclosure, the cannabinoid is made in a laboratory setting, sometimes called a synthetic cannabinoid. In one embodiment, the cannabinoid is derived or obtained from a natural source (e.g. plant) but is subsequently modified or derivatized in one or more different ways in a laboratory setting, sometimes called a semi-synthetic cannabinoid.

Within the present disclosure any reference made to a particular cannabinoid compound can also include a reference to each of the acid and/or decarboxylated forms of said particular cannabinoid.

Within the methods of the present disclosure, the step of combining the cannabinoid composition with an agent comprising a ketone functional group may be done by any suitable means including, but not limited to, mixing. In some embodiments of the present disclosure, combining the cannabinoid composition with the agent comprising a ketone functional group may provide an intermediary compound that facilitates the synthesis of CBE or an analog thereof.

As the skilled person will appreciate, a ketone is a functional group with the structures RC(=O)R', wherein R and R' may be carbon-containing substituents. In an embodiment, the agent comprising a ketone functional group is a compound comprising one or more ketone groups. In an embodiment, the compound is a symmetrical ketone whereby the substituents attached to the carbonyl center are equivalent (e.g. acetone or benzophenone). In another embodiment, the compound is an asymmetrical ketone whereby the substituents attached to the carbonyl center are not equivalent (e.g. acetophenone). In an embodiment, the compound is an unsaturated ketone, for example a ketone containing alkene and/or alkyne units (e.g. methyl vinyl ketone). In an embodiment, the compound is a cyclic ketone (e.g. cyclopropanone, cyclobutanone, cyclohexanone, or isophorone).

Non-limiting examples of ketones include acetone, oxaloacetate, diacetyl, acetyl acetone, ethyl methyl ketone (butanone), isopropyl methyl ketone, cyclohexanone, benzophenone, acetophenone, cyclopropanone, cyclobutanone, cyclohexanone, isophorone, methyl vinyl ketone, or acetophenone. In a particular embodiment, the agent comprising a ketone functional group is acetone. As the skilled person will appreciate, acetone is the commonly used name for the organic compound propanone, having the chemical formula $(CH_3)_2CO$.

In some embodiments, contacting the cannabinoid composition with an oxidizing agent may promote epoxidation. In some embodiments of the present disclosure, the oxidation agent may cause one or more of: a Shi reaction, a Sharples reaction, a Prilezhaev reaction or a Jacobsen-Katsuki reaction.

In the context of the present disclosure, the term "contacting" and its derivatives is intended to refer to bringing the cannabinoid composition, the agent comprising a ketone functional group as disclosed herein, and the oxidizing agent into proximity such that a chemical reaction can occur. In some embodiments of the present disclosure, the contacting may be by adding the oxidizing agent to the mixture of the cannabinoid composition and the agent comprising a ketone functional group. In an embodiment, the contacting is by mixing.

As used herein, the term "oxidizing agent" is intended to refer to a reactant that removes electrons from other reactants during a reaction. In some embodiments, the oxidizing agent is selected from the group consisting of persulfates, peroxides, peracids, hypochlorites, and halogens. Suitable oxidizing agents include, but are not limited to: persulfates, for example ammonium persulfates and alkali metal persulfates, including without limitation, potassium monopersulfate, lithium persulfate, sodium persulfate, and $C_4$-$C_{12}$ tetraalkylammonium persulfates (e.g. tetramethylammonium persulfate, tetraethylammonium persulfate, etc.) and tetrabutylammonium hydrogen monopersulfate; peroxides, for example hydrogen peroxide and peroxides having 1-14 carbon atoms, more particularly 4-14 carbon atoms, and more particularly still 4-8 carbon atoms, including without limitation, dibenzoyl peroxide, acetyl peroxide, propionyl peroxide, ethanyl peroxide, tertbutyl hydrogen peroxide (TBHP), and cumene hydroperoxide (CHP); peracids, being any compound including the C=C—O—O—H functional group, include for example meta-chloroperbenzoic acid (mCPBA), perdecanoic acid, magnesium monoperoxyphthalate (MMPA), and trifluroacetic acetic anhydride/Urea $H_2O_2$ (TFAA/UHP); hypochlorites, for example hypochlorite salts (e.g. sodium hypochlorite, calcium hypochlorite, lithium hypochlorite, barium hypochlorite, etc.) and esters of hypochlorous acid (e.g. tert-butyl hyochlorite); and halogens, such as for example chlorine, bromine, iodine and fluorine. In an embodiment, the oxidizing agent is potassium monopersulfate. Potassium monopersulfate is also known as potassium peroxymonosulfate and has the chemical formula $[K][HSO_5]$.

In some embodiments of the present disclosure, the method occurs at a temperature that is specified, or not, and under an inert atmosphere, or not. As used herein, the term "inert atmosphere" is intended to refer to a nonreactive gas atmosphere, such as nitrogen, argon, helium or combinations thereof. In some embodiments of the present disclosure, the temperature is between about 10° C. and about 40° C., and more particularly between about 18° C. and about 25° C. In some embodiments of the present disclosure, the temperature for the reaction is between about 20° C. and about 23° C., which is also referred to as "room temperature". In some embodiments, the temperature for the reaction is about 15° C., about 16° C., about 17° C., about 18°

C., about 19° C., about 20° C., about 21° C., about 22° C., about 23° C., about 24° C., or about 25° C.

In some embodiments of the present disclosure, the method is performed for a time between about 6 hours and about 120, and more particularly between about 12 hours and about 115 hours. In an embodiment, the time is between about 24 hours and about 96 hours. In an embodiment, the time is between about 24 hours and 48 hours. In an embodiment, the time is about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours, or about 96 hours.

As used herein, the term "product mixture" is intended to refer to the mixture formed during and/or after the methods of the present disclosure taking place. In some embodiments, the product mixture comprises the CBE or analog thereof in an amount of at least about 5 wt %, more particularly about 10 wt %, and more particularly still about 25 wt %. In select embodiments, the product mixture comprises the CBE or analog thereof in an amount of at least about 15 wt %. In select embodiments, the product mixture comprises the CBE or analog thereof in an amount of at least about 20 wt %. In select embodiments, the product mixture comprises the CBE or analog thereof in an amount of at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 96 wt %, at least 97 wt %, at least 98 wt %, or at least 99 wt %.

By "at least about X wt %" it is meant that of the total weight of the product mixture provided by the methods disclosed herein, at least that percentage is attributed to the weight of the CBE or analog thereof. In some embodiments, prior to contacting the cannabinoid composition with the oxidizing agent, the cannabinoid composition has a concentration of CBE that is lower than in the product mixture. In some embodiments, prior to contacting the cannabinoid composition with the oxidizing agent, the cannabinoid composition is free or substantially free of CBE.

In another aspect, the present disclosure provides a method for synthesizing CBE or an analog thereof, the method comprising steps of: providing a cannabinoid composition that comprises cannabidiol (CBD) or an analog thereof; combining the cannabinoid composition with an agent comprising a ketone functional group; and exposing the cannabinoid composition to electromagnetic radiation to provide a product mixture comprising CBE or an analog thereof. In embodiments of this method, the providing and combining steps may be performed as described herein in relation to the method involving the oxidizing agent.

Within the methods of the present disclosure, the step of exposing the cannabinoid composition to electromagnetic radiation may be done by any suitable means including, but not limited to, subjecting the cannabinoid composition to electromagnetic radiation provided by a lamp. In an embodiment, the electromagnetic radiation is ultraviolet (UV) radiation. In an embodiment, the UV radiation has a wavelength that is between about 100 nm and about 400 nm. The UV radiation may be within the UVA band (315-400 nm), the UVB band (280-315 nm), or the UVC band (100-280 nm). In a particular embodiment, the UV radiation has a wavelength that is between about 280 nm and about 400 nm.

In an embodiment, the method involving exposure to electromagnetic radiation is performed at the temperatures and for the times disclosed elsewhere herein.

In some embodiments, the product mixture comprises the CBE or analog thereof in an amount of at least about 5 wt %, more particularly about 10% by weight, and more particularly still about 25 wt %. In select embodiments, the product mixture comprises the CBE or analog thereof in an amount of at least about 15% by weight. In select embodiments, the product mixture comprises the CBE or analog thereof in an amount of at least about 20% by weight. In select embodiments, the product mixture comprises the CBE or analog thereof in an amount of at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 96 wt %, at least 97 wt %, at least 98 wt %, or at least 99 wt %.

In some embodiments, the cannabinoid composition has a lower concentration of CBE or analogs thereof than the product mixture. In some embodiments, the cannabinoid composition prior to the methods disclosed herein is free or substantially free of CBE or analogs thereof.

In select embodiments of the present disclosure, the methods for synthesizing CBE or analogs thereof disclosed herein further comprise a step of separating the CBE or analogs thereof from the product mixture. The separating may be by any suitable method. In select embodiments of the present disclosure, the separating comprises one or both of a chromatography step and a distillation step. In an embodiment, the chromatography step comprises a normal phase flash chromatography with a solvent system comprising heptane and one of TBME or acetone. Flash chromatography is a form of chromatography that uses low to medium pressures to push a solution through a chromatography column. The skilled person will appreciate that gravity flow or other forms of chromatography be used for the separating. In an embodiment, the distillation step comprises fractional distillation under reduced pressure. Fractional distillation separates a mixture into components based on differences in vaporization points. The skilled person will appreciate that other forms of distillation may be used to separate the CBE or analogs thereof from the product mixture.

Embodiments of the present disclosure will now be described in detail including references to FIG. 1B and FIG. 2B, which show embodiments for synthesizing CBE from a substantially CBE-free input cannabinoid composition, according to the present disclosure. General chemical reaction schematics are showing in FIG. 1A and FIG. 2A.

FIG. 1B shows a schematic for a method 100 for synthesizing CBE, the method 100 comprising the following steps: providing 110 a cannabinoid composition (A) that comprises CBD or an analog thereof; combining 120 the cannabinoid composition (A) with an agent comprising a ketone functional group (10); and contacting 130 the cannabinoid composition with an oxidizing agent (12) to provide a product mixture comprising CBE or an analog thereof (B). The skilled person will appreciate that if the cannabinoid composition (A) comprises a CBD analog, the product mixture may comprise a CBE analog.

In some embodiments of the present disclosure, the method 100 may further comprise a step of separating 140 the CBE or the analog thereof (C) from the product mixture (B) to obtain a source that has a higher purity of CBE or analog thereof (C) than the product mixture (B).

FIG. 2B shows a schematic of a method 200 for synthesizing CBE, the method 200 comprising steps of: providing 210 a cannabinoid composition (A) that comprises CBD or an analog thereof; combining 220 the cannabinoid composition (A) with an agent comprising a ketone functional group (20); and exposing 230 the cannabinoid composition to electromagnetic radiation to provide a product mixture (B) comprising CBE or an analog thereof. The skilled person will appreciate that if the cannabinoid composition (A) comprises a CBD analog, the product mixture may comprise a CBE analog.

In some embodiments of the present disclosure, the method 200 may further comprise a step of separating 240 the CBE or analog thereof (C) from the product mixture (B) to obtain a source that has a higher purity of CBE or analog thereof (C) than the mixture (B).

EXAMPLES

Example 1

CBD was dissolved in acetone in 70 mL quartz tubes to give a concentration of 5 mg/mL. The quartz tubes were placed in an RMR-600 photochemical reactor, exposed to atmosphere and kept at room temperature (about 23° C.). The reaction mixture was continuously radiated with 32 watts of UV light using lamps with a 253.7 Angstrom cut-off.

FIG. 3 shows a portion of high performance liquid chromatography (HPLC) chromatogram results over a four-day time course. FIG. 3A shows the portions of CBE and CBD detected by HPLC after one day. FIG. 3B shows the portions of CBE and CBD detected by HPLC after two days. FIG. 3C shows the portions of CBE and CBD detected by HPLC after three days. FIG. 4C shows the portions of CBE and CBD detected by HPLC after four days.

Example 2

A cannabinoid composition comprising CBD (free of CBE) was mixed with acetone and potassium monopersulfate at room temperature to produce CBE and other reaction products.

FIG. 4 shows the HPLC chromatograph results.

In the present disclosure, all terms referred to in singular form are meant to encompass plural forms of the same. Likewise, all terms referred to in plural form are meant to encompass singular forms of the same. Unless defined otherwise, all technical and scientific terms used herein have the same meaning as commonly understood by one of ordinary skill in the art to which this disclosure pertains.

As used herein, the term "about" refers to an approximately +/−10% variation from a given value. It is to be understood that such a variation is always included in any given value provided herein, whether or not it is specifically referred to.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Many obvious variations of the embodiments set out herein will suggest themselves to those skilled in the art in light of the present disclosure. Such obvious variations are within the scope of the appended claims.

The invention claimed is:

1. A method for synthesizing cannabielsoin (CBE) or an analog thereof, the method comprising mixing CBD or an analog thereof, an agent comprising a ketone functional group, and an oxidizing agent.

2. The method of claim 1, wherein the agent comprising a ketone functional group is acetone, oxaloacetate, diacetyl, acetyl acetone, ethyl methyl ketone, isopropyl methyl ketone, benzophenone, acetophenone, cyclopropanone, cyclobutanone, cyclohexanone, isophorone, or methyl vinyl ketone.

3. The method of claim 2, wherein the agent comprising a ketone functional group is acetone.

4. The method of claim 1, wherein the oxidizing agent is selected from the group consisting of persulfates, peroxides, peracids, hypochlorites, and halogens.

5. The method of claim 1, wherein the oxidizing agent is potassium monopersulfate, tetrabutylammonium hydrogen monopersulfate, hydrogen peroxide, tertbutyl hydrogen peroxide (TBHP), cumene hydroperoxide (CHP), meta-chloroperbenzoic acid (mCPBA), or sodium hypochlorite.

6. The method of claim 5, wherein the oxidizing agent is potassium monopersulfate.

7. A method for synthesizing cannabielsoin (CBE) or an analog thereof, the method comprising steps of:
    mixing cannabidiol (CBD) or an analog thereof with an agent comprising a ketone functional group; and
    exposing the mixture to electromagnetic radiation.

8. The method of claim 7, wherein the electromagnetic radiation is ultraviolet (UV) radiation.

9. The method of claim 8, wherein the UV radiation has a wavelength that is between about 100 nm and about 400 nm.

10. The method of claim 8, wherein the UV radiation has a wavelength that is between about 280 nm and about 400 nm.

11. The method of claim 7, wherein the agent comprising a ketone functional group is acetone, oxaloacetate, diacetyl, acetyl acetone, ethyl methyl ketone, isopropyl methyl ketone, benzophenone, acetophenone, cyclopropanone, cyclobutanone, cyclohexanone, isophorone, or methyl vinyl ketone.

12. The method of claim 11, wherein the agent comprising a ketone functional group is acetone.

13. The method of claim 1, wherein the CBD or an analog thereof has the structure of:

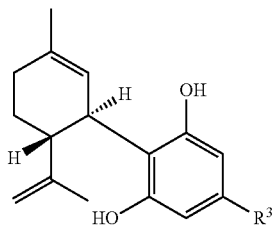

wherein $R^3$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}R^{2b}$ are each independently hydrogen or $C_1$-$C_6$ alkyl.

14. The method of claim 13, wherein $R^3$ is $C_1$-$C_{12}$ alkyl.

15. The method of claim 13, wherein $R^3$ is $C_5H_{11}$.

16. The method of claim 13, wherein $R^3$ is methyl, ethyl, propyl, butyl, heptyl, 1,1-dimethylheptyl, phenylethyl, or phenylvinyl.

17. The method of claim 7, wherein the CBD or an analog thereof has the structure of:

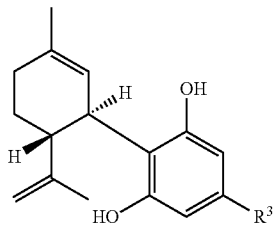

wherein $R^3$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}R^{2b}$ are each independently hydrogen or $C_1$-$C_6$ alkyl.

18. The method of claim 17, wherein $R^3$ is $C_1$-$C_{12}$ alkyl.

19. The method of claim 17, wherein $R^3$ is $C_5H_{11}$.

20. The method of claim 17, wherein $R^3$ is methyl, ethyl, propyl, butyl, heptyl, 1,1-dimethylheptyl, phenylethyl, or phenylvinyl.

* * * * *